United States Patent
Kurabayashi et al.

(10) Patent No.: US 8,437,985 B2
(45) Date of Patent: May 7, 2013

(54) SENSOR-BASED DATA FILTERING SYSTEMS

(75) Inventors: Shuichi Kurabayashi, Kanagawa (JP); Naofumi Yoshida, Kanagawa (JP); Kosuke Takano, Kanagawa (JP)

(73) Assignee: Empire Technology Development LLC, Wilmington, DE (US)

(*) Notice: Subject to any disclaimer, the term of this patent is extended or adjusted under 35 U.S.C. 154(b) by 330 days.

(21) Appl. No.: 12/645,385

(22) Filed: Dec. 22, 2009

(65) Prior Publication Data

US 2011/0153278 A1  Jun. 23, 2011

(51) Int. Cl.
*H04B 15/02* (2006.01)
*H04B 15/00* (2006.01)
*H04B 10/04* (2006.01)
*H04B 10/30* (2006.01)

(52) U.S. Cl.
USPC ............ 702/190; 702/189; 702/194; 702/197

(58) Field of Classification Search .................. 702/188, 702/190
See application file for complete search history.

(56) References Cited

U.S. PATENT DOCUMENTS

| | | | |
|---|---|---|---|
| 2005/0044393 A1* | 2/2005 | Holdsworth | 713/200 |
| 2005/0124332 A1* | 6/2005 | Clark et al. | 455/419 |
| 2008/0215609 A1* | 9/2008 | Cleveland et al. | 707/102 |
| 2010/0090802 A1* | 4/2010 | Nilsson et al. | 340/10.1 |

OTHER PUBLICATIONS

Wen, Cheng et al., Real-time ECG telemonitoring system design with mobile phone platform, Measurement, Dec. 2006, 463-470, 41 (2008), Elsevier.

Sinha, Anil-Martin et al, Multicentre evaluation of a rule-based data filter for home monitoring of implanted cardioverter defibrillators, Journal of Telemedicine and Telecare, 2006, p. 97-102, vol. 12, issue 2, London, England.

* cited by examiner

*Primary Examiner* — Michael Nghiem
*Assistant Examiner* — Felix Suarez (57) ABSTRACT

Implementations for estimating a resource usage of data-filtering program and dynamically installing the filtering programs in a sensor-based data filtering systems are generally disclosed.

17 Claims, 6 Drawing Sheets

FIG. 1

| Line No. | Filter Program |
|---|---|
| 1 | monitor (body_temperature, 60min) -> A |
| 2 | threshold (A, 100F) -> B |
| 3 | continue (B, 180 min) -> C |
| 4 | send (c) |

600 A computer program product.

602 A signal bearing medium.

604 Machine-readable instructions, which, if executed by one or more processors, operatively enable a computing device to:

receive a filter program, the filter program being defined to obtain specified data from the sensors;

dynamically install the filter program on a monitoring device; and/or     apply the filter program to data stream from the sensors.

| 606 a computer-readable medium. | 608 a recordable medium. | 610 a communications medium. |

SENSOR-BASED DATA FILTERING SYSTEMS

BACKGROUND

The technologies of medical monitoring devices are continuously progressing, thus the amount of observable data is increasing explosively. On the other hand, improving the CPU ability and/or the network bandwidth associated with such medical monitoring devices may require large-scale investments. Therefore, it may not be feasible to improve CPU ability and/or network bandwidth in synchronization with the evolution of medical monitoring devices.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to methods, apparatus, systems and/or computer program products related to filtering data. More specifically, the disclosure relates to a device, method, and/or computer program product for filtering data received from multiple sensors.

In one or more embodiments described below, a smart embedded device may be used as a telemedical monitoring device. Such a smart embedded device may include one or more sensors that may be configured to monitor a patient's physical state such as pulse, body temperature, sweating, blood pressure or the like in real time. The smart embedded device also may be configured to transmit such monitoring data to a remote system for a doctor to monitor the patient via a network. In order to monitor physical states of the patient who has a certain disease in real time from a remote site, it may be useful to select the required data appropriately according to a given treatment strategy, considering physical or logical limitation of the system resource such as CPU capability, network bandwidth and/or the like.

Figure 1:
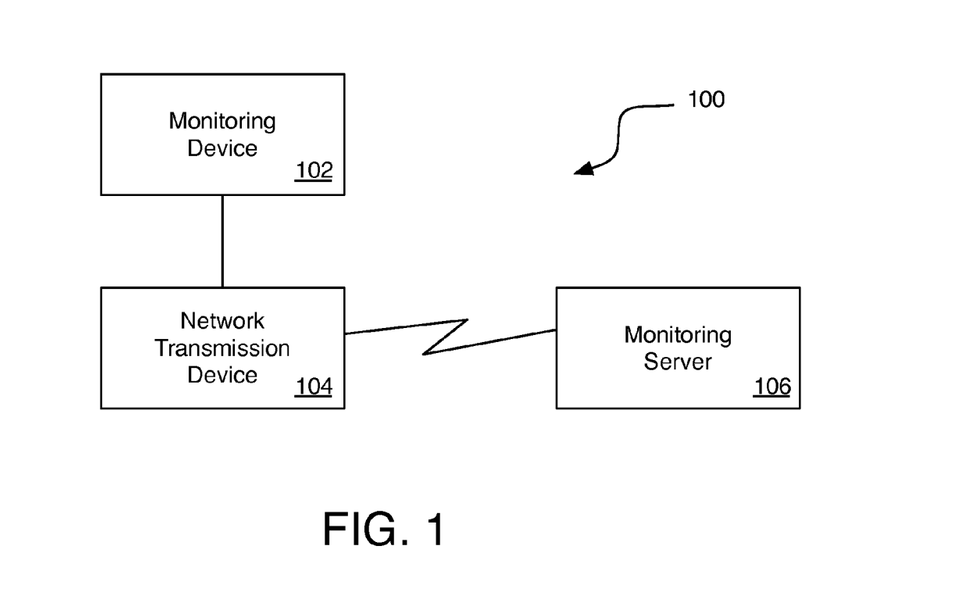
FIG. 1 illustrates a schematic of an example telemedical monitoring system 100 for monitoring a specific condition of a patient from a remote site.

FIG. 1 shows a schematic of a telemedical monitoring system 100 for monitoring a specific condition of a patient from a remote site in accordance with at least some embodiments of the present disclosure. This telemedical monitoring system 100 may include a smart embedded device 102 used as a monitoring device associated with a network transmission device 104 (e.g. a WiFi-enabled PDA, cellular phone or the like) and a monitoring server 106. Such a smart embedded device 102 may communicate with the monitoring server 106, by using the network transmission device 104.

The smart embedded device 102 may have a capability to monitor physical states of a patient who is equipped with such a smart embedded device 102. The smart embedded device 102 may be configured to measure several physical data, such as a pulse, body temperature, perspiration, blood pressure, the like, or combinations thereof. The smart embedded device 102 may be configured to transmit such monitoring data to the monitoring server 106 by using the associated network transmission device 104 (e.g. cellular phone) that may support a broadband network connection, such as TCP/IP over 3G or the like.

In order to select necessary data appropriately from the sensor monitoring data according to the treatment strategy, a filter program may be installed on the smart embedded device 102.

The filter program is a set of sequential instruction operators defined to obtain necessary data from the sensors. For example, the filter program may be designed according to a treatment strategy for a patient who has a certain disease.

Figure 2:
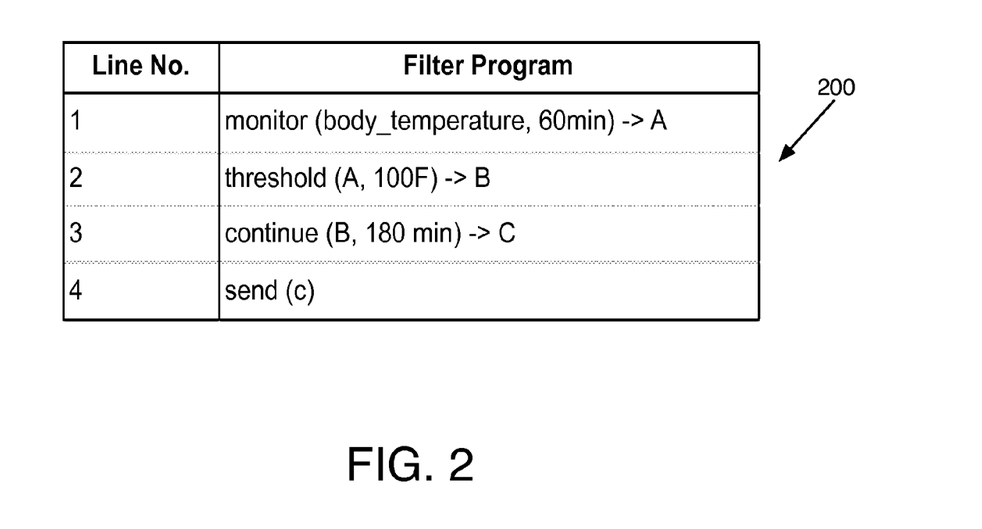
FIG. 2 illustrates a table of an example of a filter program.

FIG. 2 shows an example of a filter program 200 in accordance with at least some embodiments of the present disclosure. Such a filter program 200 may include a set of sequential instruction operators defined to obtain necessary data from sensors (not shown) of smart embedded device 102 (FIG. 1). Such a filter program 200 may be designed according to one or more treatment strategies for a patient who has a certain disease.

In the illustrated example a thermal sensor equipped to the patient may be monitored, and monitoring data of body temperature may be transmitted to a monitoring server 106 (FIG. 1) (e.g. a doctor's server). For example, monitoring data of body temperature may be transmitted to the monitoring server 106 (FIG. 1) in cases where the body temperature stays over 100° F. for three hours. In this example of filter program 200, four filtering instruction operators may be used, which may include monitor, threshold, continue, and send. At line 1, the monitor function may access the thermal sensor at 60 minutes intervals. At line 2, the threshold function may check the retrieved body temperature, and may output the result data in cases where the body temperature is over 100° F. At line 3, the continue function may check the result of threshold, and may output the result data in cases where the data streams keeps its state during 180 minutes. Finally, at line 4, the send function may send the extracted data, which means that the patient has had a high body temperature for 3 hours (180 minutes), to the monitoring server 106 (FIG. 1).

In this example, the filter program 200 may be designed and created at the monitoring server 106 (FIG. 1), based at least in part on the treatment strategy for the patient. The filter program 200 may include parameters and configuration information, such as selection of sensors and frequency of sensor monitoring. Additionally, the monitoring server 106 (FIG. 1) may send the filter program to the smart embedded device 102 (FIG. 1) via network transmission device 104 (FIG. 1). In another embodiment, the filter program 200 may be stored in a storage media (not shown) such as CD-ROM or the like and provided a user or a patient.

Figure 3:
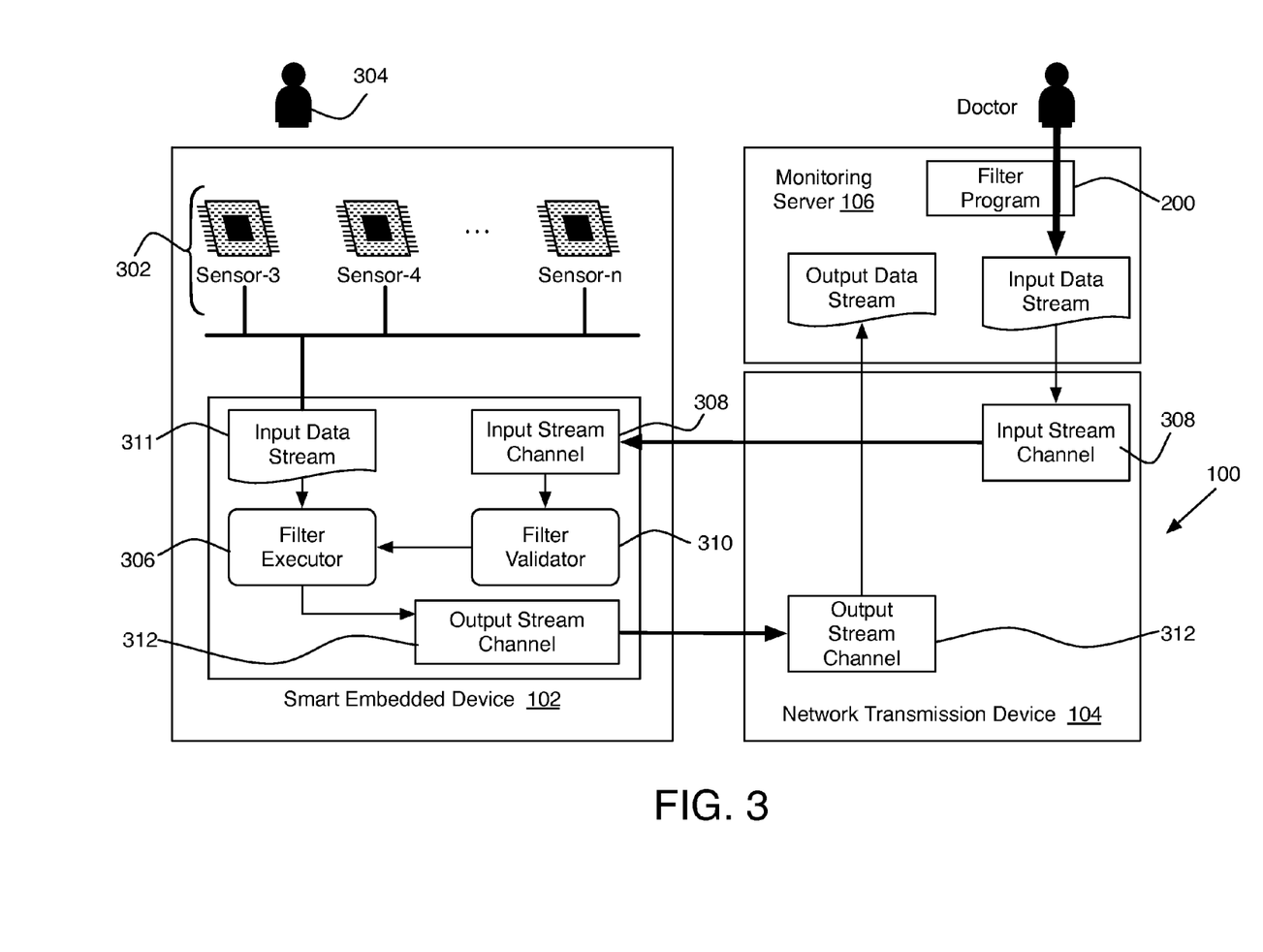
FIG. 3 illustrates a schematic diagram of an example telemedical monitoring system.

FIG. 3 shows the architectural overview of the telemedical monitoring system 100 for medical diagnosis in accordance with at least some embodiments of the present disclosure. This telemedical monitoring system 100 may include the smart embedded device 102, the network transmission device 104, and the monitoring server 106. The smart embedded device 102 may have one or more sensors 302 (e.g. sensor chips) for monitoring a physical state of a patient 304. The smart embedded device 102 may be configured to receive the filter program 200 from the remote monitoring server 106. Such a filter program 200 may be configured to obtain specified data from the sensors 302 of the smart embedded device 102. The smart embedded device 102 may receive the filter program 200 from the remote monitoring server 106 by using the network transmission device 104. The remote monitoring server 106 and the smart embedded device 102 may be operatively connected via network transmission device 104 through an input stream channel 308. In another embodiment, the smart embedded device 102 may receive the filter program 200 from a storage media.

The smart embedded device 102 may include two computation modules. One computation module may include a filter executor 306 that may be configured to apply an installed filter program 200 to input data streams 311 received from the one or more sensors 302. Accordingly, the smart embedded device 102 may operate both as a "data filtering device" and/or as a "monitoring device," and may be referred to in these terms below. For example, the filter program 200 may include a set of sequential instruction operators configured to obtain specified data from the sensors 302. The filter program 200 may include a parameter configured to select some or all of sensors 302 to use for obtaining specified data. Further, the filter program 200 may include additional parameters configured to define a frequency of sensor monitoring. In some examples, the filter executor 306 may be configured to invoke the filter program 200 in response to a predetermined condition being detected by the sensors 302.

Another computation module may include a filter validator 310 configured to check whether the install filter programs 200 can run on the smart embedded device 102 or not (e.g., installable or not). The sensors 302 may write the observed data into an input data stream 311 for the filter executor 306 in which filter program 200 may be installed. The filter executor 306 may generate the selected data. For example, the filter executor 306 may be configured to apply the filter program 200 to a data stream from the sensors 302. The smart embedded device 102 may transmit the selected data to the monitoring server 106 (e.g. a doctor's server) by using network transmission device 104. The network transmission device 104 and the smart embedded device 102 may be operatively connected via an output stream channel 312.

The filter executor 306 may apply an installed filter program 200 to input data streams 311 received from the one or more sensors 302. The filter executor 306 may have basic instruction operators set for data filtering. Such a filter program 200 may be programmed by using these instruction operators. Thus, in one example, a filter program 200 can be defined as a sequential set of instruction operators.

The filter executor 306 may be configured to invoke such a filter program 200 in response to change of physical state of a patient 304. For example, when a pulse value exceeds a predetermined value, the filter executor 306 may invoke the filter program 200 to select data and transmit data to the monitoring server 106. For example, the filter executor 306 may invoke the filter program 200 to select data and transmit data to the monitoring server 106 through the Internet in real time. Additionally, the filter program 200 may keep running for a given time span, until a specific state of patient is detected, or some other condition is met.

The filter validator 310 may estimate a computing resource requirement for executing a given filter program 200 and may decide whether or not the filter program 200 can run on the smart embedded device 102. For example, the filter validator 310 may be configured to estimate the computing resource requirement associated with an execution of the filter program 200 and may be configured to decide if the filter program 200 is installable—in other words, the filter program 200 can run on the smart embedded device 102. The computing resource requirement may include mobile network bandwidth, CPU usage, temperature of the smart embedded device 102, maximum power consumption, main memory size, secondary storage size, acceptable frequency of disk access, or the like. By the filter validator 310 estimating a computing resource requirement dynamically, the telemedical monitoring system 100 may execute multiple filter programs 200 simultaneously. Thus, the availability or capacity of computing resources changes dynamically according to the number and types of installed filtering programs. In some embodiments, the filter validator 310 may further include a resource requirement profile that may be configured to store resource requirement information for the usage of the sensors 302.

In cases where the filter validator 310 decides that the smart embedded device 102 has enough computing resources for the filter program 200, e.g. the filter program 200 can run on the smart embedded device 102, the filter validator 310 may install the filter program 200 into the filter executor 306. For example, filter validator 310 may be configured to receive the filter program 200 and may be configured to dynamically install the filter program 200, where the filter program 200 may have been defined to obtain specified data from the sensors 302.

The telemedical monitoring system 100 can provide a "dynamic installation and invocation mechanisms" for a filter program 200. Because attaching and detaching a smart embedded device 102 to patients may be highly time consuming, telemedical monitoring system 100 may be utilized to install and customize a filter program 200 or a data analysis program dynamically in such a smart embedded device 102 while keeping the smart embedded device equipped to the patient 304. By using the smart embedded device 102, the monitoring server 106 (e.g. the doctor's server) can retrieve appropriate data from the sensor devices in a highly flexible manner.

In cases where the filter validator 310 decides that the smart embedded device 102 does not have enough computing resources for the filter program 200, i.e. the filter program 200 is non-installable; the filter validator 310 may be configured to invoke a notification procedure to report the failure of installation. Additionally or alternatively, such a notification procedure may further report the resource requirement for the filter program 200. Such reports of the failure of installation and/or the resource requirement for the filter program 200 may be sent to the monitoring server 106 via the network transmission device 104, which may be configured to transmit data selected by the filter program 200 using a network interface.

In such a notification, the filter validator 310 may provide the information of the required computing resources for the filter program 200 and available computing resources in order to prompt a doctor to change the parameters in the filter program 200 to adapt the filter program 200 to the available computing resources of the smart embedded device 102. In another embodiment, the filter validator 310 may provide the information of the required computing resources for more than one filter program 200 (e.g. every filter program 200) existing on the device, in order to prompt a doctor to uninstall or change the unnecessary existing filter programs 200.

Figure 4:
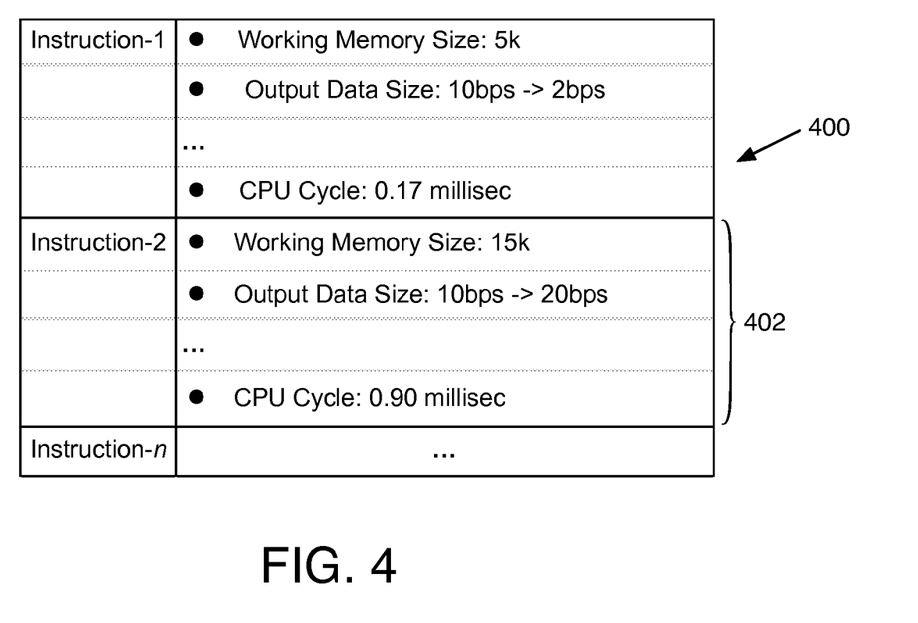
FIG. 4 illustrates a table of example resource requirement profiles for individual instruction operators.

FIG. 4 shows examples of resource requirement profiles 400 for individual instruction operators in accordance with at least some embodiments of the present disclosure. The filter validator 310 (FIG. 3) may include a set of resource requirement profiles 400 that may be utilized to estimate the resource requirement for a filter program 200 (FIG. 3). Individual resource requirement profiles 402 may store resource requirement information (e.g. working memory size, CPU cycle required to execute the filter program, memory usage required to execute the filter program, memory usage required to store data resulting from execution of the filter program, power consumption of the sensors, heat value of the sensors, or the like) for the execution of individual instruction operators respectively. For example, the filter program 200 (FIG. 3) may include a set of sequential instruction operators configured to obtain specified data from the sensors 302 (FIG. 3), and the filter validator 310 (FIG. 3) may include a resource requirement profile 402 configured to store resource requirement information to execute individual instruction operators.

By referencing these profiles 400, the filter validator 310 (FIG. 3) can estimate the required computation resources for execution of a filter program 200 (FIG. 3). The filter validator 310 (FIG. 3) may check the capability to run the filter program 200 (FIG. 3) within the current available computing resources.

Referring back to FIG. 3, the filter validator 310 may further include a set of resource requirement profiles associated with sensors 302. Individual resource requirement profiles associated with sensors 302 may store resource requirement information (e.g. power consumption, heat value, or the like) for the usage of sensors 302. By referencing these profiles, the filter validator 310 can estimate the resource requirement for execution of filter programs 200. The filter validator 310 may check the capability to run the filter program 200 within the current available computing resources.

Thus, the disclosed system can provide the following two estimation functions. Equation (1) includes a resource estimation function defined as follows:

$$f\_est(o, p\_1, p\_2, \ldots, p\_n) \rightarrow <c, t, r> \quad (1)$$

where "o" represents the size of input data; p_1, p_2, . . . , p_n represent a set of parameters for a target operator to be estimated; "c" represents a required CPU cycle for executing the operator; "t" represents a required working memory which occupies memory area temporary when the operator is running; and "r" represents a required working memory for return value of the operator.

Equation (2) includes a resource estimation function for sensor devices defined as follows:

$$f\_(est\_sensor)(freq) \rightarrow <e, s> \quad (2)$$

where "freq" represents a frequency of monitoring a sensor; "e" represents a power consumption in the sensor device according to the monitoring frequency; and "s" represents a temperature of the sensor device according to the monitoring frequency.

The filter validator 310 may further compute several additional parameters by using the above five (5) values (c, t, r, e, and/or s). For example, the filter validator 310 may further compute an additional parameter "N" representing a required network bandwidth that is computed according to the estimated output data size (e.g. a sum of r). The filter validator 310 may further compute an additional parameter "SS" representing a required space for the secondary storage. Parameter SS may be computed according to the output data size (r) and the monitoring frequency (freq). The filter validator 310 may further compute an additional parameter "WF" representing an estimated frequency of write access to the secondary storage. Parameter WF may be computed according to the output data size (r) and the monitoring frequency (freq).

Accordingly, the filter validator 310 can check the capability to run the filter program 200 within the current available computing resources.

Figure 5:
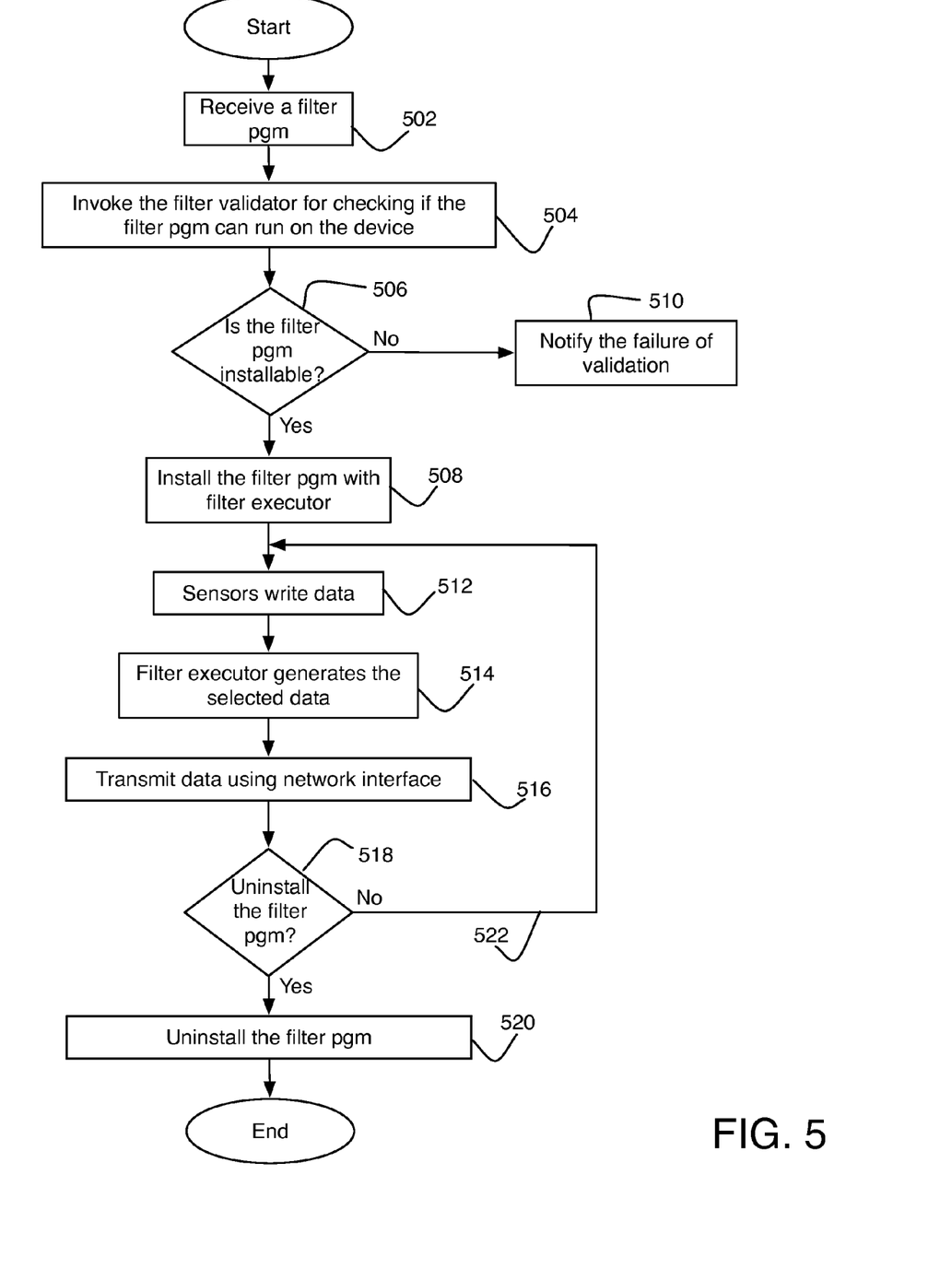
FIG. 5 illustrates an example process for filtering data on the smart embedded device.

FIG. 5 shows a flow diagram illustrating a method of filtering data on the smart embedded device in accordance with at least some embodiments of the present disclosure. Process 500, and other processes described herein, set forth various functional blocks or actions that may be described as processing steps, functional operations, events and/or acts, etc., which may be performed by hardware, software, and/or firmware. Those skilled in the art in light of the present disclosure will recognize that numerous alternatives to the functional blocks shown in FIG. 5 may be practiced in various implementations. For example, although process 500, as shown in FIG. 5, comprises one particular order of blocks or actions, the order in which these blocks or actions are presented does not necessarily limit claimed subject matter to any particular order. Likewise, intervening actions not shown in FIG. 5 and/or additional actions not shown in FIG. 5 may be employed and/or some of the actions shown in FIG. 5 may be eliminated, without departing from the scope of claimed subject matter.

At operation 502, the smart embedded device 102 (FIG. 3) may receive a filter program 200 (FIG. 3) from a remote monitoring server 106 (FIG. 3) via a network. Such a filter program 200 (FIG. 3) may be configured to obtain specified data from the sensors 302 (FIG. 3) of the smart embedded device 102 (FIG. 3). In another embodiment, the smart embedded device 102 (FIG. 3) may receive the filter program 200 (FIG. 3) from a storage media.

At operation 504, the smart embedded device 102 (FIG. 3) may invoke the filter validator 310 (FIG. 3) for checking if the filter program 200 (FIG. 3) can run on the device the smart embedded device 102 (FIG. 3). The filter validator 310 (FIG. 3) may estimate the required computing resources for executing the filter program 200 (FIG. 3) by analyzing the functions (instruction operators) used in the filter programs 200 (FIG. 3).

Such an operation may be utilized to ensure outputting the processed results within a limited time "t", consistent with equation (3) below:

$$P(f,m,n)<t \quad (3)$$

where "P" represents a function for computing execution time; "f" represents a processing time for a sensor data; "n" represents a frequency of monitoring sensors, "m" represents a number of sensor devices; and "t" represents the specified time (e.g. the limited time.

For example, "P" may be expressed in equation (4) as follows:

$$m*(Pt+Nt)*n<t \quad (4)$$

where "m" represents a number of sensor devices; "Pt" represents a processing time for a tuple of sensor data; "Nt" represents an uploading time for a tuple of sensor data; and "n" represents a frequency of monitoring sensors.

In one example where m=5, Pt=0.001 seconds, Nt=0.01 seconds, and t=3.0 seconds, equation (4) can be written as follows:

$$5*(0.001+0.01)*n<3.0,$$

where n=545 (e.g. the frequency of monitoring sensors). Such an operation may be utilized to ensure outputting the sensor data within the limited time (3.0 sec.) by computing the frequency of monitoring sensors to be analyzed. The following factors may be considered as computing resources: mobile network bandwidth, CPU usage, temperature of the smart embedded device 102 (FIG. 3), maximum power consumption, main memory size, secondary storage size, acceptable frequency of disk access, or the like. Please note that for medical use, the maximum temperature of the smart embedded device 102 (FIG. 3) may be limited to avoid harming the patient's physical/mental health. In one example, a Current SSD (Solid State Drive), which may be used as a secondary storage of smart embedded devices 102 (FIG. 3), may include a limitation in write (erase) cycles. For example, SSD cells may wear out after 1,000 to 10,000 write cycles for multi-level cell (MLC). Process 500 may reduce the monitoring frequency of sensor devices to extend the life of an SSD by reducing the write access to the SSD.

At operation 506, the filter validator 310 (FIG. 3) may decide if the smart embedded device 102 (FIG. 3) has enough computing resources for the filter program 200 (FIG. 3). For example, the filter validator 310 (FIG. 3) may decide if installable conditions would result from usage of the filter program 200 (FIG. 3).

At operation 508, in cases where the filter validator 310 (FIG. 3) determines that the smart embedded device 102 (FIG. 3) has enough computing resources for the filter program 200 (FIG. 3) (e.g. the filter program is installable), the filter validator 310 (FIG. 3) may install the filter program 200 (FIG. 3) into the filter executor 306 (FIG. 3). Process 500 may then proceed to operation 512. For example, the filter validator 310 (FIG. 3) may "dynamically" install the filter program 200 (FIG. 3) on the smart embedded device 102 (FIG. 3). Accordingly, the telemedical monitoring system 100 (FIG. 3) can provide a "dynamic installation and invocation mechanisms" for the filter program 200 (FIG. 3). Because attaching and detaching a smart embedded device 102 (FIG. 3) to patients may be highly time consuming, telemedical monitoring system 100 (FIG. 3) may be utilized to install and customize the filter program 200 or a data analysis program dynamically in such a smart embedded device 102 (FIG. 3) while keeping the smart embedded device 102 (FIG. 3) equipped to the patient. By using telemedical monitoring system 100 the monitoring server 106 (FIG. 3) can retrieve appropriate data from the smart embedded device 102 (FIG. 3) in a highly flexible manner.

At operation 510, in cases where the filter validator 310 (FIG. 3) determines that the smart embedded device 102 (FIG. 3) does not have enough computing resources for the filter program 200 (FIG. 3), a notification may be sent to the monitoring server 106 (FIG. 3) that the filter validation was failed.

Proceeding from operation 508, at operation 512, the one or more sensors 302 (FIG. 3) may write the observed data into the input data stream 311 (FIG. 3) for the filter executor 306 (FIG. 3).

At operation 514, the filter executor 306 (FIG. 3) may generate selected data. For example, the smart embedded device 102 (FIG. 3) may apply the filter program 200 (FIG. 3) to the input data stream 311 (FIG. 3) from the sensors 302 (FIG. 3).

At operation 516, the smart embedded device 102 (FIG. 3) may transmit the selected data for the monitoring server 106 (FIG. 3) by using a network interface, such as via output stream channel 312 (FIG. 3).

At operation 518, the filter validator 310 (FIG. 3) may check if the smart embedded device 102 (FIG. 3) receives an instruction to uninstall the filter program 200 (FIG. 3) from the smart embedded device 102 (FIG. 3).

At operation 520, in cases where such an instruction to uninstall the filter program 200 (FIG. 3) is received via the smart embedded device 102 (FIG. 3), the filter validator 310 (FIG. 3) may uninstall the filter program 200 (FIG. 3) from the smart embedded device 102 (FIG. 3).

At operation 522, in cases where such an instruction to uninstall the filter program 200 (FIG. 3) is not received via the smart embedded device 102 (FIG. 3), the filter program 200 (FIG. 3) may keep running. For example, the process 500 may return to an earlier operation, such as operation 512, or the like.

Figure 6:
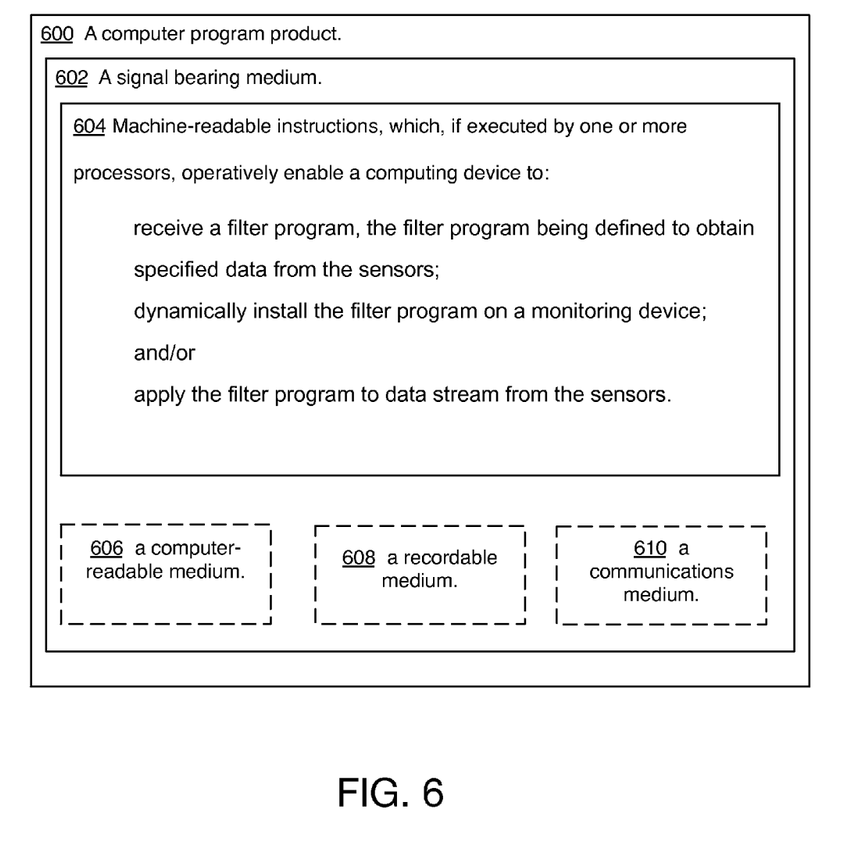
FIG. 6 illustrates an example computer program product.

FIG. 6 illustrates an example computer program product 600 that is arranged in accordance with the present disclosure. Program product 600 may include a signal bearing medium 602. Signal bearing medium 602 may include one or more machine-readable instructions 604, which, if executed by one or more processors, may operatively enable a computing device to provide the functionality described above with respect to FIG. 5. Thus, for example, referring to the system of FIG. 1, Monitoring device 102 and/or network transmission device 104 may undertake one or more of the actions shown in FIG. 5 in response to instructions 604 conveyed by medium 602.

In some implementations, signal bearing medium 602 may encompass a computer-readable medium 606, such as, but not limited to, a hard disk drive, a Compact Disc (CD), a Digital Versatile Disk (DVD), a digital tape, memory, etc. In some implementations, signal bearing medium 602 may encompass a recordable medium 608, such as, but not limited to, memory, read/write (R/W) CDs, R/W DVDs, etc. In some implementations, signal bearing medium 602 may encompass a communications medium 610, such as, but not limited to, a digital and/or an analog communication medium (e.g., a fiber optic cable, a waveguide, a wired communications link, a wireless communication link, etc.).

Figure 7:
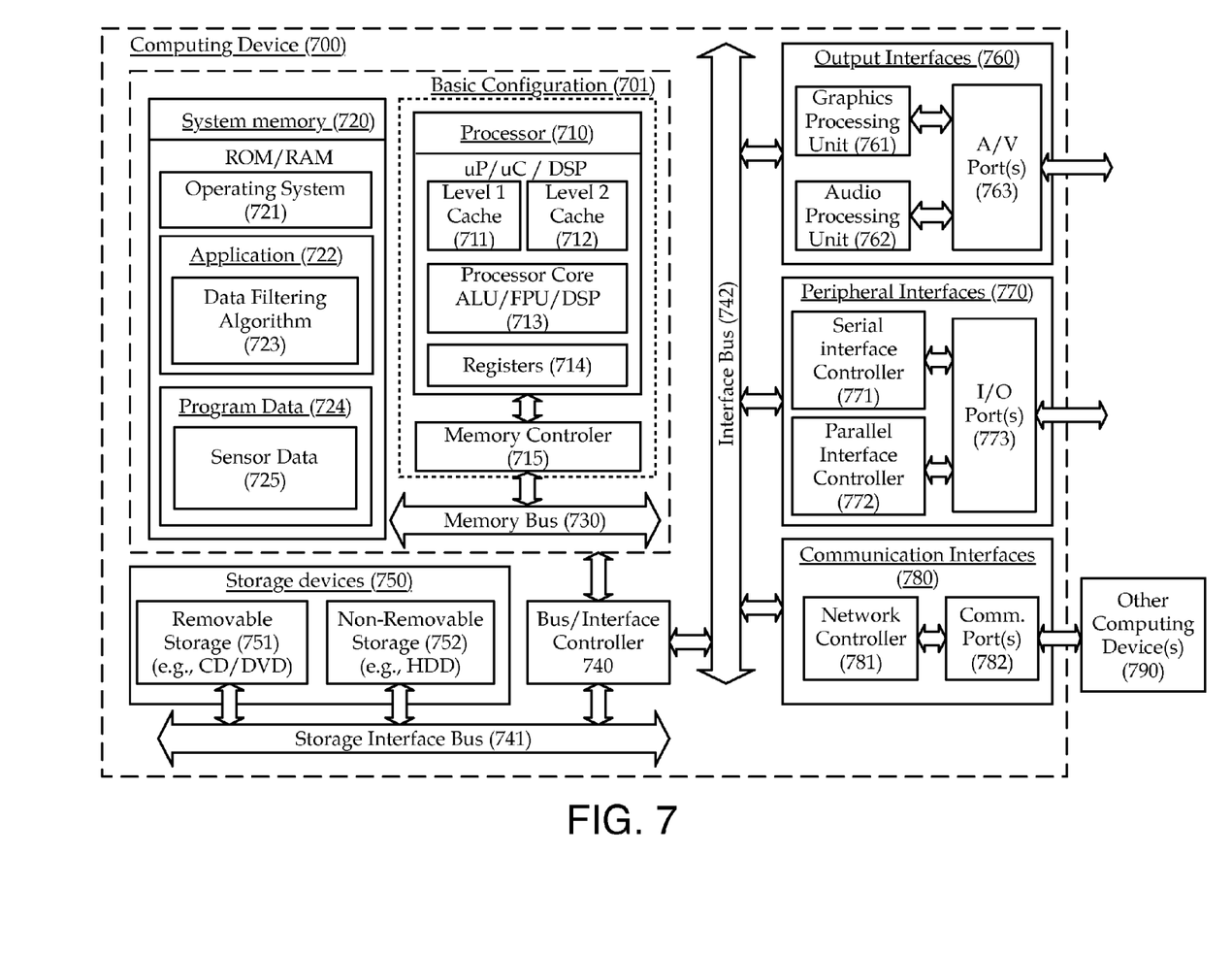
FIG. 7 is a block diagram illustrating an example computing device, all arranged in accordance with the present disclosure.

FIG. 7 is a block diagram illustrating an example computing device 700 that is arranged in accordance with the present disclosure. In one example configuration 701, computing device 700 may include one or more processors 710 and system memory 720. A memory bus 730 can be used for communicating between the processor 710 and the system memory 720.

Depending on the desired configuration, processor 710 may be of any type including but not limited to a microprocessor (µP), a microcontroller (µC), a digital signal processor (DSP), or any combination thereof. Processor 710 can include one or more levels of caching, such as a level one cache 711 and a level two cache 712, a processor core 713, and registers 714. The processor core 713 can include an arithmetic logic unit (ALU), a floating point unit (FPU), a digital signal processing core (DSP Core), or any combination thereof. A memory controller 715 can also be used with the processor 710, or in some implementations the memory controller 715 can be an internal part of the processor 710.

Depending on the desired configuration, the system memory 720 may be of any type including but not limited to volatile memory (such as RAM), non-volatile memory (such as ROM, flash memory, etc.) or any combination thereof. System memory 720 may include an operating system 721, one or more applications 722, and program data 724. Application 722 may include a data filtering algorithm 723, such as the filter program 200 (FIG. 3) for utilization by in a telemedical monitoring system 100 (FIG. 3) that is arranged to perform the functions and/or operations as described herein including the functional blocks and/or operations described with respect to process 500 of FIG. 5. Program Data 724 may include sensor data 725 for use in a data filtering algorithm 723. In some example embodiments, application 722 may be arranged to operate with program data 724 on an operating system 721 such that implementations of sensor-based data filtering may be provided as described herein. This described basic configuration is illustrated in FIG. 7 by those components within dashed line 701.

Computing device 700 may have additional features or functionality, and additional interfaces to facilitate communications between the basic configuration 701 and any required devices and interfaces. For example, a bus/interface controller 740 may be used to facilitate communications between the basic configuration 701 and one or more data storage devices 750 via a storage interface bus 741. The data storage devices 750 may be removable storage devices 751, non-removable storage devices 752, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 720, removable storage 751 and non-removable storage 752 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 700. Any such computer storage media may be part of device 700.

Computing device 700 may also include an interface bus 742 for facilitating communication from various interface devices (e.g., output interfaces, peripheral interfaces, and communication interfaces) to the basic configuration 701 via the bus/interface controller 740. Example output interfaces 760 may include a graphics processing unit 761 and an audio processing unit 762, which may be configured to communicate to various external devices such as a display or speakers via one or more A/V ports 763. Example peripheral interfaces 760 may include a serial interface controller 771 or a parallel interface controller 772, which may be configured to communicate with external devices such as input devices (e.g., keyboard, mouse, pen, voice input device, touch input device, etc.) or other peripheral devices (e.g., printer, scanner, etc.) via one or more I/O ports 773. An example communication interface 780 includes a network controller 781, which may be arranged to facilitate communications with one or more other computing devices 790 over a network communication via one or more communication ports 782. A communication connection is one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR) and other wireless media. The term computer readable media as used herein may include both storage media and communication media.

Computing device 700 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 700 may also be implemented as a personal computer including both laptop computer and non-laptop computer configurations. In addition, computing device 700 may be implemented as part of a wireless base station or other wireless system or device.

Some portions of the foregoing detailed description are presented in terms of algorithms or symbolic representations of operations on data bits or binary digital signals stored within a computing system memory, such as a computer memory. These algorithmic descriptions or representations are examples of techniques used by those of ordinary skill in the data processing arts to convey the substance of their work to others skilled in the art. An algorithm is here, and generally, is considered to be a self-consistent sequence of operations or similar processing leading to a desired result. In this context, operations or processing involve physical manipulation of physical quantities. Typically, although not necessarily, such quantities may take the form of electrical or magnetic signals capable of being stored, transferred, combined, compared or otherwise manipulated. It has proven convenient at times, principally for reasons of common usage, to refer to such signals as bits, data, values, elements, symbols, characters, terms, numbers, numerals or the like. It should be understood, however, that all of these and similar terms are to be associated with appropriate physical quantities and are merely convenient labels. Unless specifically stated otherwise, as apparent from the following discussion, it is appreciated that throughout this specification discussions utilizing terms such as "processing," "computing," "calculating," "determining" or the like refer to actions or processes of a computing device, that manipulates or transforms data represented as physical electronic or magnetic quantities within memories, registers, or other information storage devices, transmission devices, or display devices of the computing device.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In some embodiments, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a flexible disk, a hard disk drive (HDD), a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will+ be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A data filtering device, comprising:
    a plurality of sensors;
    a transmission device;
    a filter validator configured to:

receive a filter program, the filter program being defined to obtain data (d) from one or more sensors (m) of the plurality of sensors at a specified frequency (f) and transmit the obtained data using the transmission device, estimate a resource requirement associated with an execution of the filter program, the resource requirement being estimated according to the following formula:

$$m*(Pt+Nt)*f,$$

with Pt being the time required to obtain the date (d) and Nt being the time required to transmit the of obtained data, decide if the filter program is installable based at least in part on the estimated resource requirement, and install the filter program; and a filter executor configured to apply the filter program to a data stream from the plurality of sensors.

2. A data filtering device as recited in claim 1, wherein the filter program includes a set of sequential instruction operators configured to obtain data from the one or more sensors.

3. A data filtering device as recited in claim 1, wherein the filter program includes a parameter configured to select the one or more sensors to use for obtaining data.

4. A data filtering device as recited in claim 3, wherein the filter program further includes a second parameter configured to define the frequency.

5. A data filtering device as recited in claim 1, wherein the filter executor is configured to invoke the filter program in response to a predetermined condition being detected by one or more sensors.

6. A data filtering device as recited in claim 1, wherein the filter program includes a set of sequential instruction operators configured to obtain data from the one or more sensors, and the filter validator includes a resource requirement profile configured to store resource requirement information and to execute individual instruction operators.

7. A data filtering device as recited in claim 6, wherein the filter validator further includes a resource requirement profile configured to store resource requirement information for the usage of at least one of the plurality of sensors.

8. A data filtering device as recited in claim 1, wherein the filter validator is configured to install the filter program, if the filter validator decides the filter program is installable.

9. A data filtering device as recited in claim 1, wherein the filter validator is configured to invoke a notification procedure to report a failure of installation, if the filter validator decides the filter program is not installable.

10. A data filtering device as recited in claim 9, wherein the notification procedure further reports the resource requirement for the filter program.

11. A data filtering device as recited in claim 6, wherein the resource requirement information includes a CPU cycle required to execute the filter program.

12. A data filtering device as recited in claim 6, wherein the resource requirement information includes memory usage required to execute the filter program.

13. A data filtering device as recited in claim 6, wherein the resource requirement information includes memory usage required to store data resulting from execution of the filter program.

14. A data filtering device as recited in claim 7, wherein the resource requirement information includes power consumption of at least one of the plurality of sensors.

15. A data filtering device as recited in claim 7, wherein the resource requirement information includes heat value of at least one of the plurality of sensors.

16. A data filtering method used on a monitoring device comprising a plurality of sensors, the method comprising:

receiving, via the monitoring device, a filter program, the filter program being configured to obtain data (d) from one or more sensors (m) of the plurality of sensors at a specified frequency (f);

estimating a resource requirement associated with an execution of the filter program, the resource requirement being estimated according to the following formula:

$$m*(Pt+Nt)*f,$$

with Pt being the time required to obtain the data (d) and Nt being the time required to transmit the obtained data;

deciding if the filter program is installable based at least in part on the estimated resource requirement;

dynamically installing the filter program on the monitoring device; and applying, via the monitoring device, the filter program to a data stream from the plurality of sensors.

17. An article comprising:

a non-transitory signal bearing medium comprising machine-readable instructions stored thereon, which, if executed by one or more processors, operatively enable a computing-type monitoring device comprising a plurality of sensors to:

receive a filter program, the filter program being defined to obtain data (d) from one or more sensors (m) of the plurality of sensors at a specified frequency (f);

estimate resource requirement associated with an execution of the filter program, the resource requirement being estimated according to the following formula:

$$m*(Pt+Nt)*f,$$

with Pt being the time required to obtain the data (d) and Nt being the time required to transmit the obtained data;

decide if the filter program is installable based at least in part on the estimated resource requirement;

dynamically install the filter program on the monitoring device; and apply the filter program to a data stream from the plurality of sensors.

* * * * *